(12) United States Patent
Edwards

(10) Patent No.: US 7,425,658 B2
(45) Date of Patent: Sep. 16, 2008

(54) PROCESS FOR PRODUCING 1-OCTENE FROM BUTADIENE

(75) Inventor: Charles Lee Edwards, Houston, TX (US)

(73) Assignee: Shell Oil Company, Houston, TX (US)

( * ) Notice: Subject to any disclaimer, the term of this patent is extended or adjusted under 35 U.S.C. 154(b) by 768 days.

(21) Appl. No.: 10/887,697

(22) Filed: Jul. 9, 2004

(65) Prior Publication Data

US 2005/0038305 A1 Feb. 17, 2005

Related U.S. Application Data

(60) Provisional application No. 60/494,212, filed on Aug. 11, 2003.

(51) Int. Cl.
C07C 2/04 (2006.01)
C07C 1/207 (2006.01)

(52) U.S. Cl. ............... 585/329; 585/324; 585/502; 585/638

(58) Field of Classification Search ........... 585/329, 585/324, 502, 638
See application file for complete search history.

(56) References Cited

U.S. PATENT DOCUMENTS

| | | | |
|---|---|---|---|
| 4,180,694 A | 12/1979 | Nozaki | 585/511 |
| 4,229,605 A | 10/1980 | Nozaki | 585/509 |
| 4,229,606 A | 10/1980 | Nozaki | 585/509 |
| 4,687,876 A | 8/1987 | Nozaki | 585/509 |
| 5,030,792 A | 7/1991 | Slaugh | 585/639 |
| 5,198,598 A | 3/1993 | Hill et al. | 568/619 |
| 5,412,137 A | 5/1995 | Prashad et al. | 558/146 |
| 5,872,272 A | 2/1999 | Yano et al. | 556/12 |
| 2003/0235550 A1 | 12/2003 | Pan et al. | 424/70.16 |

FOREIGN PATENT DOCUMENTS

| | | |
|---|---|---|
| EP | 0218100 A1 | 4/1987 |
| EP | 0278407 A2 | 8/1988 |
| EP | 1178029 A1 | 2/2002 |
| GB | 2114974 A | 9/1983 |
| WO | 90/13531 | 11/1990 |
| WO | WO 92/10450 | 6/1992 |
| WO | WO9302032 | 2/1993 |
| WO | 94/14822 | 7/1994 |
| WO | 02/062732 A1 | 8/2002 |

OTHER PUBLICATIONS

"Selective Synthesis of Octadienyl and Butenyl Ethers Via Reaction of 1,3-Butadiene With Alcohols Catalyzed by Homogeneous Palladium Complexes," by Renata Patrini et al., *Journal of Molecular Catalysis A: Chemical* 129 (1998) pp. 179-189.
"Palladium-catalyzed telomerization of butadiene with ethylene glycol in liquid single phase and biphasic systems: control of selectivity and catalyst recycling" by Arno Behr, Michael Urschey, *Journal of Molecular Catalysis A, Chemical*, vol. 197 (Apr. 18, 2003) pp. 101-113.
"Sex Pheromones of Summerfruit Tortrix Moth, Adoxophyes Orana 2. Compounds Influencing Their Attractant Activity" by S. Voerman and A. K. Minks, *Environmental Entomology, Entomological Society of America*, vol. 2, No. 5, (Oct. 15, 1973)pp. 750-756.
"Allylation Using Allylborates" by Roger Hunter, *Tetrahedron*, Elsevier Science Publishers, Amsterdam, Netherlands, vol. 50, No. 3, (1994) pp. 871-888.
International Search Report of Feb. 23, 2005.
Written Opinion for PCT/US2004/025815 dated Feb. 23, 2005.
U.S. Appl. No. 10/887,736, filed Jul. 9, 2004, Edwards.
International Search Report of Feb. 18, 2004.
Written Opinion of PCT/US2004/025814 of Feb. 18, 2004.

*Primary Examiner*—Thuan Dinh Dang

(57) ABSTRACT

Method for producing 1-octene from butadiene by dimerizing and alkoxylating butadiene in the presence of one or more alkoxy substituted phosphine ligands under alkoxydimerization conditions with an alkoxydimerization catalyst, the alkoxydimerization conditions being effective to produce an alkoxydimerization product with one or more alkoxy substituted octadienes comprising primarily 1-alkoxy substituted octadiene; hydrogenating the alkoxydimerization product under hydrogenation conditions effective to produce a hydrogenation product which is primarily 1-alkoxy substituted octane; eliminating the alkoxy group from the hydrogenation product under elimination conditions effective to produce an elimination product which is primarily 1-octene and a first alkanol having from about 1 to about 3 carbon atoms; and separating the 1-octene from said elimination product.

201 Claims, No Drawings

PROCESS FOR PRODUCING 1-OCTENE FROM BUTADIENE

FIELD OF THE APPLICATION

This application claims the benefit of U.S. Provisional Application No. 60/494,212 filed Aug. 11, 2003, the entire disclosure of which is hereby incorporated by reference.

The application relates to a new, economical process for producing 1-octene from butadiene.

BACKGROUND

A high demand exists for alpha olefins ("1-olefins" or "1-alkenes"), such as 1-octene and 1-decene. Many processes for producing alpha olefins use ethylene—a high cost feedstock—and produce other, less desirable olefin by-products. New processes are needed to economically produce relatively pure alpha olefins.

SUMMARY OF THE APPLICATION

The application provides a method for producing 1-octene from butadiene. The method comprises:
dimerizing and alkoxylating butadiene in the presence of one or more alkoxy substituted phosphine ligands under alkoxydimerization conditions comprising an alkoxydimerization catalyst, the alkoxydimerization conditions being effective to produce an alkoxydimerization product comprising one or more alkoxy substituted octadienes comprising primarily 1-alkoxy substituted octadiene;
hydrogenating the alkoxydimerization product under hydrogenation conditions effective to produce a hydrogenation product comprising primarily 1-alkoxy substituted octane;
eliminating the alkoxy group from the hydrogenation product under elimination conditions effective to produce an elimination product comprising primarily 1-octene and a first alkanol having from about 1 to about 3 carbon atoms; and, separating the 1-octene from said elimination product.

DETAILED DESCRIPTION

The present application provides a process for producing 1-octene from butadiene. The process basically comprises: a combined dimerization and alkoxy-substitution of the diolefin to produce an alkoxy substituted octadiene (preferably methoxy-substituted octadiene); hydrogenation of the alkoxy substituted octadiene to alkoxylated octane (preferably methoxylated octane); and, elimination of the alkoxy group to produce the corresponding alkanol (preferably methanol) and 1-octene. The process is economically attractive because (a) the conversion efficiency is high, and (b) butadiene and alkanol are relatively inexpensive starting materials.

The general scheme is shown below:

In the foregoing scheme:
R is selected from the group consisting of alkyl groups having from about 1 to about 3 carbon atoms, preferably methyl groups;
X is an alkoxydimerization catalyst comprising a noble metal;
Y is an alkoxy substituted phosphine ligand;
Z is a hydrogenation catalyst comprising one or more metals;
Δ is a source of energy, preferably heat, which is effective to eliminate the alkoxy substituent from the remainder of the alkoxy substituted molecule, producing alkanol and 1-octene; and,
Z' is an elimination catalyst effective to enhance the elimination of the alkoxy substituent.

Combined Dimerization and Alkoxy-Substitution of the Butadiene to Produce an Alkoxy Substituted Octadiene The dimerization and alkoxy-substitution of the butadiene occur during the same reaction, herein called the "alkoxydimerization process." In order to perform the alkoxydimerization process, an alkanol, the alkoxydimerization catalyst, and the butadiene are mixed. It is possible to mix the butadiene with the alkanol and thereafter to add the ligand(s) discussed below. However, it is preferable to add the ligand(s) to the alkanol, to mix the alkoxydimerization catalyst with the resulting alkanol/ligand solution, to activate the catalyst, and then to add the butadiene.

Suitable alkanols have from about 1 to about 3 carbon atoms. A most preferred alkanol is methanol. The alkanol serves as a solvent and a reactant.

Suitable ligands are effective to promote the formation of a product comprising primarily the 1-alkoxy substituted octadiene. In a preferred embodiment, the ligands are effective to form a product comprising 90 wt. % or more of the 1-alkoxy substituted octadiene, preferably greater than 90 wt. % of the 1-alkoxy substituted octadiene, more preferably greater than 93 wt. % of the 1-alkoxy substituted octadiene, and most preferably 95 wt. % or more of the 1-alkoxy substituted octadiene. In a most preferred embodiment, the ligands also are effective to stabilize the catalyst. This is evidenced by a reduction in (or the absence of) deposition of noble metal onto the reactor walls during the reaction when compared to the same reaction performed in the absence of the ligand. The quantity of ligand preferably is from about 0.8 moles to about 1.2 moles.

Preferred ligands include, but are not necessarily limited to alkoxy substituted phosphine ligands, preferably alkoxy substituted phenyl phosphine ligands. Alkoxy substituted phenyl phosphine ligands are effective to prevent decomposition of the alkoxydimerization catalyst. Preferred alkoxy substituted phenyl phosphine ligands include, but are not necessarily limited to tris-(2,4,6,trimethoxy phenyl)phosphine and tris-(4-methoxyphenyl)phosphine. A most preferred ligand is tris-(4-methoxyphenyl)phosphine.

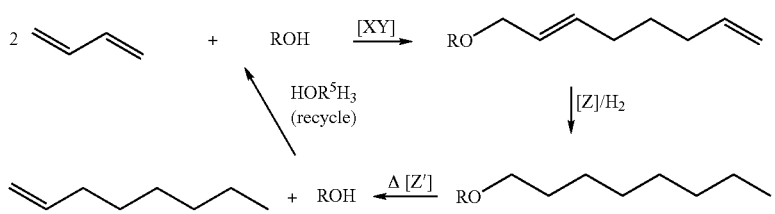

The alkanol and the ligands are mixed using any suitable conditions to produce an alkanol/ligand solution. Preferably, the ligands are added to the alkanol and the mixture is agitated.

In a preferred embodiment, the alkoxydimerization catalyst is mixed with the alkanol/ligand solution to produce an alkoxydimerization catalyst mixture. The alkoxydimerization catalyst comprises a noble metal. Suitable noble metals for the alkoxydimerization catalyst include but are not necessary limited to platinum, palladium, iridium, rhenium, ruthenium, and osmium. Preferred noble metals include, but are not necessarily limited to palladium, platinum, and ruthenium. A most preferred noble metal for the alkoxydimerization catalyst is palladium.

The alkoxydimerization catalyst preferably is a salt of a noble metal. The noble metal salt may be soluble or superficially insoluble in the alkanol or alkanol/ligand mixture. By "superficially insoluble" is meant that the alkoxydimerization catalyst comprises salt(s) which appear to be insoluble in the alkanol or alkanol/ligand mixture, but which apparently produce "noble metal moieties" which are catalytically effective.

Without being bound by any particular theory unless claimed, the chemical transformations that involve the alkoxydimerization catalyst are quite complex, probably involving the formation and destruction of complexes between the noble metal salt or noble metal moieties, the butadiene, and/or the presumed butadiene dimer intermediate. The formation of catalytically effective noble metal moieties is believed to be influenced by interaction of the alkoxydimerization catalyst with the butadiene, the presumed butadiene dimers, and/or the alkanol. To obtain optimum reaction rates, the alkoxydimerization catalyst preferably is an alkanol-soluble noble metal salt.

Suitable salts of the noble metal are organic or inorganic acids. Illustrative examples include the halide and oxalate salts. Also suitable are salts wherein the metal is present in the anion as, for example, chloropalladate salt or chloroplatinate salts. Metal complexes also are suitable, such as metal complexes with tertiary nitrogen-containing ligands. The known τ-allyl complexes are also suitably used. Most preferred alkoxydimerization catalysts comprises two noble metal atoms per molecule. Such alkoxydimerization catalysts include, but are not necessarily limited to tris(dibenzylideneacetone)di noble metal. A preferred alkoxydimerization catalyst is tris(dibenzylideneacetone)dipalladium. The alkoxydimerization catalyst may be provided fresh and/or as a recycled stream from the alkoxydimerization (or telomerization) process.

Only catalytic quantities of the noble metal are required. Although a larger amount of alkoxydimerization catalyst is not detrimental to the process, the amount used generally is sufficient to produce an alkoxydimerization catalyst mixture comprising from about 0.005% mole to about 0.1% mole noble metal, based on total reactants, preferably from about 0.01% mole to about 0.05% mole noble metal.

The alkoxydimerization catalyst mixture is exposed to "activation conditions" effective (a) to dissolve reactants other than the alkoxydimerization catalyst, and (b) to activate the alkoxydimerization catalyst. The result is an "activated catalyst mixture." The activation conditions comprise maintaining the alkoxydimerization catalyst mixture at an "activation temperature" for a period of time effective to activate the catalyst (referred to as the "activation time"). If the alkoxydimerization catalyst is an alkanol soluble noble metal salt, then the activation temperature and the activation time are effective to dissolve the noble metal salt in the alkanol/ligand solution. If the alkoxydimerization catalyst is superficially alkanol insoluble, then the activation temperature and activation time are effective to liberate "noble metal compound moieties" in the alkanol/ligand solution.

A suitable activation temperature is about 0° C. or more, preferably about 25° C. The activation time preferably is as short as possible, limited primarily by practical constraints. A suitable activation time is about 1 minute or more. A preferred activation time is about 10 minutes. The method of mixing is not critical, although some agitation decreases the activation time.

Butadiene preferably is added to the activated catalyst mixture. The butadiene may be obtained from any known source. The amount of butadiene added is effective to produce an optimum butadiene:alkanol mole ratio. The optimum butadiene:alkanol mole ratio depends in part upon the specific alkanol and the desired conversion. A butadiene:alkanol mole ratio of as low as about 1:5 is suitable if low conversion is desired. To obtain higher conversion, a more substantial proportion of butadiene is preferred and the butadiene:alkanol mole ratio is from about 1:3 to about 1:0.5. Best results are obtained when the butadiene:alkanol mole ratio is from about 1:2 to about 1:1.

It is possible to use other solvents in the reaction mixture as long as those solvents are inert to the reactants. However, the use of additional solvent other than the alkanol is not preferred. If another solvent is deemed advisable, suitable solvents are those listed below as suitable for hydrogenation.

In a preferred embodiment, butadiene is added to the activated catalyst mixture. Because the addition of butadiene to the activated catalyst mixture generally produces an exothermic reaction, the activated catalyst mixture preferably is cooled to a preliminary temperature sufficiently low to control the exothermic reaction. The butadiene is added to this cooled activated catalyst mixture. Preferably, the temperature of the cooled activated catalyst mixture is about 0° C. or less, preferably to about −60° C. The butadiene-containing cooled activated catalyst mixture is the "final alkoxydimerization mixture."

The final alkoxydimerization mixture is slowly heated to a preliminary temperature of about 60° C. or less, preferably about 25° C. or less, preferably with agitation. Thereafter, the final alkoxydimerization mixture is heated to and maintained at an alkoxydimerization temperature effective to produce about 90 wt. % or more of the 1-alkoxy substituted octadiene. A preferred alkoxydimerization temperature is about 60° C. The alkoxydimerization temperature is maintained for an alkoxydimerization time of about 2 hours or more, preferably about 8 hours or less, more preferably about 6 hours or less, most preferably about 4 hours.

Typical alkoxydimerization pressures vary from about 5 atmospheres to about 20 atmospheres. Frequently, good results are obtained when the alkoxydimerization pressure is autogenous, or when the alkoxydimerization pressure is the pressure generated when the reactants are maintained at the alkoxydimerization temperature in a sealed reaction vessel. Such pressures are from about 1 atmosphere to about 20 atmospheres.

Once the alkoxydimerization time has passed, the final alkoxydimerization mixture is cooled, preferably to the preliminary temperature, most preferably to about 25° C. or less. The cooled final alkoxydimerization product is depressurized. The cooled final alkoxydimerization product may be fed directly to hydrogenation, or the alkoxylated octadienes may be recovered and fed to hydrogenation. Recovery of the alkoxylated octadienes is accomplished using any suitable conventional means, such as selective extraction, fractional distillation and chromatographic techniques.

In a preferred embodiment, the yield of the desired 1-alkoxy substituted octadiene is 90 wt. % or more, preferably greater than 90 wt. %, more preferably greater than 93 wt. %, and most preferably 95 wt. % or more.

Hydrogenation of the Alkoxy Substituted Octadiene to an Alkoxylated Octane

Because the alkoxydimerization catalyst comprises a noble metal, it is possible to perform the hydrogenation using the alkoxydimerization catalyst. However, greater efficiency is achieved when the alkoxydimerization product is separated and fed to a hydrogenation reactor comprising a fixed bed hydrogenation catalyst. Substantially any of the known heterogeneous or homogeneous hydrogenation catalysts may be used. Preferred hydrogenation catalysts are heterogeneous hydrogenation catalysts.

Suitable hydrogenation catalysts comprise a metal having an atomic number of from 26 to 78, which includes but is not necessarily limited to Fe, Co, Ni, Cu, Zn, Ga, Ge, As, Se, Br, Kr, Rb, Sr, Y, Zr, Nb, Mo, Tc, Ru, Rh, Pd, Ag, Cd, In, Sn, Sb, Te, I, Xe, Cs, Ba, the lanthanide series (comprising Ce, Pr, Nd, Pm, Sm, Eu, Gd, Th, Dy, No, Er, Tm, Yb, Lu), Hf, Ta, W, Re, Os, Ir, Pt. Preferred metals for the hydrogenation catalyst have an atomic number of 28 to 78 [Ni, Cu, Zn, Ga, Ge, As, Se, Br, Kr, Rb, Sr, Y, Zr, Nb, Mo, Tc, Ru, Rh, Pd, Ag, Cd, In, Sn, Sb, Te, I, Xe, Cs, Ba, the lanthanide series (comprising Ce, Pr, Nd, Pm, Sm, Eu, Gd, Tb, Dy, No, Er, Tm, Yb, Lu), Hf, Ta, W, Re, Os, Ir, Pt]. Other known catalysts suitable for hydrogenation include the oxides and sulfides of Group VI, including but not necessarily limited to Cr, Mo and W.

The hydrogen may be provided as pure hydrogen or the hydrogen may be diluted with one or more additional gases. Suitable additional gases are inert, and do not interfere with the hydrogenation process. For example, it may be desirable to use a process gas, such as syngas, to supply the required hydrogen. Such a process gas is suitable for use as the hydrogen source as long as the process gas does not interfere with the hydrogenation process.

The hydrogenation is either a batch process or a continuous process, preferably continuous. In a batch process, a homogeneous or heterogeneous catalyst is charged to the reactor along with the reactants and the reactor is pressured with hydrogen, or a hydrogen-containing gas. In a continuous process the hydrogenation catalyst preferably is a packed bed of solid catalyst, more preferably a supported metal catalyst, and the alkoxy substituted octadienes and hydrogen are simultaneously passed through the bed, which is maintained at hydrogenation conditions.

The reactor is maintained at hydrogenation conditions comprising a hydrogenation temperature and a hydrogenation time, the hydrogenation conditions being effective to hydrogenate the alkoxy substituted octadienes and to produce primarily alkoxy substituted octanes. Hydrogenation temperatures generally are from about 0° C. to about 100° C., preferably about 50° C. A suitable hydrogenation time generally is about 4 hours, preferably about 1 hour. Typical hydrogenation pressures are from about atmospheric pressure to about 10 bar or higher.

The hydrogenation is conducted in the presence or absence of a solvent. If a solvent is used, the solvent preferably is inert to the hydrogenation conditions. Suitable solvents include, but are not necessarily limited to ethers, aromatic hydrocarbons, paraffins, halogenated hydrocarbons, and nitriles.

Suitable ethers include, but are not necessarily limited to dialkyl ethers, alkyl aryl ethers, cyclic ethers, and lower alkyl ethers. Example of such ethers include, but are not necessarily limited to dibutyl ether, methyl hexyl ether, anisole, phenyl butyl ether, tetrahydrofuran, dioxane, dioxolane, ethylene glycol dimethyl ether, diethylene glycol dimethyl ether, tetraethylene glycol dimethyl ether, and glycol triethyl ether. Suitable aromatic hydrocarbons include, but are not necessarily limited to benzene, toluene, and xylene. Suitable halogenated hydrocarbons include, but are not necessarily limited to chloroform, carbon tetrachloride, tetrachloroethylene, methylene chloride and bromoform. Suitable sulfoxides include, but are not necessarily limited to dimethylsulfoxide. Suitable nitriles include but are not necessarily limited to acetonitrile and benzonitrile.

Elimination of the Alkoxy Group

The alkoxylated octane produced by hydrogenation is subjected to elimination conditions effective to eliminate the alkoxy group in the form of an alkanol, thereby producing 1-octene. Although the elimination reaction may be performed in the absence of an elimination catalyst, it is preferred to use an elimination catalyst effective to increase the yield of 1-octene.

Suitable elimination catalysts include, but are not necessarily limited to selected metal oxides and metal oxides doped with a metal selected from the group consisting of Li, Na, K, Rb, and Cs and combinations thereof. Preferred elimination catalysts are selected from the group consisting of Cs-doped alumina, preferably Cs-doped alpha alumina, zinc oxide, and combinations thereof. A most preferred elimination catalyst is zinc oxide.

Preferred elimination catalysts have a mesh size effective to maximize surface area without clogging the system. A preferred alpha alumina for use in the Cs-doped alpha alumina is 57105 carrier, which is commercially available from Zeolyst Corporation (57105 carrier). A preferred zinc oxide is HTZ-4, which is commercially available from Holdor Topsoe Corporation.

The elimination is performed in any suitable reactor adapted to provide the necessary gas and reactant flows and temperature. A preferred reactor is a hot tube reactor.

In a preferred embodiment, the reactor containing the elimination catalyst is purged with an inert gas. Suitable inert gases include, but are not necessarily limited to such as nitrogen or argon. The inert gas preferably is introduced downflow at a flow rate effective to purge air from the system. Suitable flow rates are from about 1 to about 10 ml/min., preferably about 6.2 ml/min.

The reactor is heated to an elimination temperature. The elimination selectivity to 1-octene varies depending upon several factors, including but not necessarily limited to the elimination catalyst and the elimination temperature. Generally, the conversion increases with an increase in elimination temperature, but selectivity decreases with an increase in elimination temperature. The elimination temperature preferably is selected to maximize both conversion and selectivity to 1-octene.

Commercially acceptable selectivity to 1-octene is 80 mole % or more, preferably 90 mole % or more. Commercially acceptable conversions are those that achieve high levels of selectivity to 1-octene. Conversion as high as 20 mole % can produce selectivities greater than 90 mole %. Methanol and 1-octene easily are separated from the reaction mixture, and any unconverted alkoxy octane preferably is recycled to the reactor, preferably a hot tube reactor.

Preferred elimination temperatures vary with the composition of the elimination catalyst. Where the elimination catalyst is Cs-doped alpha alumina, suitable temperatures are from about 350° C. to about 600° C., preferably from about 400° C. to about 550° C. Where the elimination catalyst is zinc oxide, suitable temperatures are from about 250° C. to about 400° C., preferably from about 250° C. to about 300° C., more preferably about 250° C.

In a most preferred embodiment, the elimination catalyst is zinc oxide and the elimination temperature is about 250° C. This combination has demonstrated elimination conversion of 20 mole % or more, and selectivity to 1-octene of 90 mole % or more.

Suitable pressures for the elimination are from about 0.8 atm to 1.2 atm, preferably about 1.0 atm.

The elimination produces an elimination product comprising alkanol and 1-octene. The 1-octene is separated from the elimination product using suitable means, including but not necessarily limited to distillation. Preferably, the 1-octene is separated by distillation. Unreacted alkoxylated alkane and alkanol preferably are recycled to the appropriate location. For example, the alkanol is recycled to the alkoxydimerization process.

Ranges and limitations other than those specified herein that perform substantially the same function in substantially the same manner to obtain the same or substantially the same result are within the scope of the specification and the claims.

The process will be illustrated by the following examples, which are provided for illustration only and are not intended to limit the scope of the invention.

Alkoxydimerization of Butadiene

The parameters and results of the alkoxydimerization experiments are given in the following Table, and the experiments are described in more detail below:

EXAMPLE 1

A total of 1 gram (0.0045 moles) of palladium acetate was dissolved in 50 ml of dry toluene and placed in a 500 ml Zipperclave (316 s.s.) autoclave. The reaction mixture was placed under $N_2$ by evacuation and refilling with $N_2$. The reaction mixture was stirred for 10 minutes at 25° C. in order to dissolve all material. Then the reaction mixture was cooled to −60° C. at which time 100 grams (1.85 moles) of butadiene was transferred to the autoclave from the butadiene feed tank. The reaction mixture was allowed to slowly come to 25° C. with stirring and then heated to 60° C. for 8 hours. The reaction was cooled to 25° C. and depressured. There was considerable deposition of Pd metal on the walls of the reactor.

The contents were transferred to a separatory funnel and the catalyst removed by water washing and extraction with salt water. The crude reaction mixture was analyzed by GC. After removal of unreacted butadiene and toluene solvent, a total of 33 grams of a mixture of two acetoxyoctadiene isomers was recovered. Of this mixture, there was 93% w 1-acetoxy-2,7-octadiene (the desired intermediate) and 7% w 3-acetoxy-1,7-octadiene.

EXAMPLE 2

Example #1 was repeated exactly with the exception of using tris(dibenzylideneacetone)di palladium(O) as the palladium catalyst. (Since this compound has two palladium metals per molecule, it produces 2 moles of Pd in solution for every mole used). The molar concentration of Pd catalyst was

| Example No. | Source of Pd catalyst | Pd cat. (mole) | Ligand (moles) | Adduct (g) | Solvent (50 ml) | T (° C.) | Time (hrs) | Yield (g) | % wt 1-isomer | % wt 3-isomer |
|---|---|---|---|---|---|---|---|---|---|---|
| 1 | acetate | 0.0045 | none | HOAc (53) | Toluene | 60 | 8 | 33 g | 93 | 7 |
| 2 | dba* | 0.001 | none | HOAc (53) | Toluene | 60 | 8 | 13 g | 95 | 5 |
| 3 | Acetate | 0.0045 | (phenyl)3P** (0.0045) | HOAc (53) | Toluene | 60 | 8 | 25 g | 85 | 15 |
| 4 | Dba | 0.001 | (CycloHexyl)3P (0.002) | HOAc (53) | Toluene | 60 | 8 | <1 g | — | — |
| 5 | Dba | 0.001 | (n-Bu)3N (0.002) | HOAc (53) | Toluene | 60 | 8 | 15 g | 95 | 5 |
| 6 | Acetate | 0.0045 | none | HOAc (53) | Cyclohexane | 60 | 8 | 17 g | 94 | 6 |
| 7 | Acetate | 0.0045 | None | HOAc (100) | None | 60 | 8 | 11 g | 94 | 4 |
| 8 | Acetate | 0.0045 | Benzy(phenyl)2 P (0.0045) | HOAc (53) | Toluene | 60 | 8 | 15 g | 84 | 16 |
| 9 | Acetate | 0.0045 | Et(phenyl)2P (0.0045) | HOAc (53) | Toluene | 60 | 8 | 24 g | 83 | 17 |
| 10 | Acetate | 0.0045 | (2,4,6-trimethoxy phenyl)3P (0.0045) | HOAc (53) | Toluene | 60 | 8 | 17 g | 93 | 7 |
| 11 | Acetate | 0.0045 | (4-methoxyphenyl)3P (0.0045) | HOAc (53) | Toluene | 60 | 8 | 26 g | 92 | 8 |
| 12 | Dba | 0.001 | (4-methoxyphenyl)3P (0.002) | MeOH (100) | none | 60 | 4 | 94 g | 96 | 4 |
| 13 | Dba | .00028 | (4-methoxyphenyl)3P (0.00056) | MeOH (100) | none | 60 | 4 | 82 g | 95 | 5 |
| 14 | Dba | .00028 | (4-methoxyphenyl)3P (0.00028) | MeOH (100) | none | 60 | 4 | 110 g | 96 | 4 |

*"dba" refers to "dibenzylideneacetone".
**"2P, 3P and the like refers to the number of phosphine groups.

~½ that of the previous Example but produced a similar result. Isolation of the product afforded 13 grams of a mixture of isomers (95% wt 1-isomer and 5% wt 3-isomer). Again, there was considerable deposition of Pd metal on the walls of the reactor.

EXAMPLE 3

Example #1 was repeated exactly with the exception that triphenylphosphine was used as a ligand in conjunction with the palladium metal catalyst. The triphenylphosphine was added to the toluene solvent prior to addition of the palladium acetate. An orange complex was produced. This mixture, containing the triphenylphosphine and palladium acetate dissolved in the toluene was introduced to the autoclave as in Example #1. At the end of the reaction, considerably less palladium metal was observed to be deposited on the walls of the reactor. Isolation of the acetoxyoctadienes afforded 25 grams of two products (85% of the 1-acetoxy-2,7-octadiene and 15% wt of the 3-acetoxy-1,7-octadiene).

EXAMPLE 4

Example #2 was repeated exactly with the exception of using tricylcohexylphosphine as a ligand associated with the palladium. No product was isolated using this system.

EXAMPLE 5

Example #2 was repeated exactly with the exception of using tri-n-butylamine as a ligand associated with the palladium. The results of this Example were almost identical to that of Example #2 indicating that there was no effect of using this amine ligand on the final results of the Example.

EXAMPLE 6

Example #1 was repeated exactly with the exception of using cyclohexane as solvent. The amount of product isolated was reduced somewhat, but the isomeric ratio was the same.

EXAMPLE 7

Example #1 was repeated exactly with the exception that no additional solvent was used. Instead, twice the concentration of HOAc was used. The amount of product isolated was reduced somewhat, but the isomeric ratio was the same.

EXAMPLE 8

Example #3 was repeated except that benzyldiphenylphosphine was used as the ligand instead of triphenylphosphine. The results were essentially the same.

EXAMPLE 9

Example #3 was repeated except that ethyldiphenylphosphine was used as the ligand instead of triphenylphosphine. The results were essentially the same.

EXAMPLE 10

Example #3 was repeated except that tris-(2,4,6-trimethoxyphenyl)phosphine was used as the ligand instead of triphenylphosphine. The resulting acetoxyoctadienes were 93% wt 1-isomer and 7% wt 3-isomer, a marked improvement over the trialkylphosphines used previously. The overall yield was similar to the trialkylphosphines.

EXAMPLE 11

Example #3 was repeated except that tris-(4-methoxyphenyl)phosphine was used as the ligand instead of triphenylphosphine. The overall yield was improved (26 grams) and the resulting acetoxyoctadienes were 92% wt 1-isomer and 8% wt 3-isomer. Here again, a marked improvement was obtained using alkoxyphenylphosphines compared to using the trialkylphosphines used previously.

EXAMPLE 12

Example #1 was repeated using the same equipment and general procedures but with the following exceptions: Tris (dibenzylideneacetone)di palladium(O) was used as the palladium catalyst, tris-(4-methoxyphenyl)phosphine was used as the ligand and 100 ml of methanol was used in place of acetic acid and toluene solvent. While attempting to heat to 60° C. (the normal reaction temperature) a strongly exothermic reaction occurred which required cooling with chilled water to the reactor. Due to the strong exothermic nature of the reaction, the total reaction time was reduced from the normal 8 hours to 4 hours. Isolation of the orange product mixture afforded 94 grams of a mixture of methoxyoctadienes (96% wt 1-somer and 4% 3-isomer). There was very little evidence of palladium metal decomposition on the walls of the reactor.

EXAMPLE 13

Example #12 was repeated exactly except that the amount of catalyst and ligand was decreased by ⅓. There was a small exotherm and the total reaction time used was 4 hours. Isolation of the product mixture afforded 82 grams of methoxyoctadienes (95% wt 1-methoxy-2,7-octadiene and 5% wt 3-methoxy-1,7-octadiene).

EXAMPLE 14

Example #13 was repeated exactly except that the amount of ligand was decreased by ½. There was a small exotherm and the total reaction time used was 4 hours. Isolation of the product mixture afforded 110 grams of methoxyoctadienes (96% wt 1-methoxy-2,7-octadiene and 4% wt 3-methoxy-1,7-octadiene).

Hydrogenation of Alkoxylated Butadiene

EXAMPLE 15

A total of 0.5 gram 5% wt palladium supported on barium sulfate was added to 150 grams of a mixture of 97% wt 1-methoxy-2,7-octadiene and 3% wt 3-methoxy-1,7-octadiene and this slurry mixture placed in a 500 ml Zipperclave (316 s.s.) autoclave. The reaction mixture was placed under $N_2$ by evacuation and refilling with $N_2$. Then hydrogen gas was added to the stirred slurry until an atmosphere of 300 psig $H_2$ as achieved. The reaction mixture was maintained at 25-35° C. (the reaction was exothermic) by addition of cooling water. The reaction was stirred for 3 hours. The pressure on the reactor was reduced and the catalyst removed from the product mixture by filtration. Analysis of the product mixture by NMR showed the absence of any olefinic material and the mixture to contain 97% wt 1-methoxyoctane and 3% wt 3-methoxyoctane. The colorless product weighed 151 grams.

EXAMPLE 16

To a 500 ml. Zipperclave (316 s.s) was added 150 grams of a mixture of 96% 1-methoxy-2,7-octadiene and 4% 3-methoxy-1,7-octadiene. The powdered palladium catalyst (0.5 g of 5% wt Pd/BaSO$_4$) was added in one portion. The reaction was placed under N$_2$ by evacuation and refilling with N$_2$. The reaction mixture was then stirred at 25° C. at which time H$_2$ was introduced to the reactor. The initial pressure was 50 psig H$_2$ which caused an exotherm. The reaction temperature was controlled by cooling to maintain ~35° C. As the reaction began to slow the pressure was increased slowly to a total pressure of 100 psig H$_2$. The reaction was finished by 2 hours at which time there was no further uptake of H$_2$. The reaction mixture was cooled and the pressure vented. The reaction mixture was filtered to remove catalyst producing a clear, colorless liquid that upon analysis showed complete hydrogenation. This mixture was used for de-methanolysis reactions.

Elimination of Alkanol to Produce 1-Octene

The parameters and results of the elimination experiments are given in the following Table, and the experiments are described in more detail below:

EXAMPLE 19

Example 17 was repeated with the exception that the temperature was 550° C. Under these conditions 1-methoxyoctane was converted to 1-octene in 2 m % selectivity at 12 m % conversion.

EXAMPLE 20

Example 17 was repeated with the exception that an alpha alumina (14-20 mesh) obtained from Zeolyst Corporation (57105 carrier) was used as catalyst, the N$_2$ flow was adjusted to 16.3 ml/min and temperature of 400° C. employed. Under these conditions 1-methoxyoctane was converted to 1-octene in 76 m % selectivity at 17 m % conversion. When the temperature was increased to 500° C., 1-methoxyoctane was converted to 1-octene in 65 m % selectivity at 27 m % conversion.

EXAMPLE 21

Example 1 was repeated with the exception that a zinc oxide (14-20 mesh) obtained from Holdor Topsoe Corporation (HTZ-4) was used as catalyst, the N$_2$ flow was adjusted to

| Example | Catalyst | 1-MO Flow Rate (ml/min) | N$_2$ Flow Rate (ml/min) | Temp. (° C.) | 1-MO Conversion (% m) | Selectivity to 1-octene (% m) | Selectivity to internal octane (% m) |
|---|---|---|---|---|---|---|---|
| 16 | SiC | 0.1 | 6.2 | 450 | 3.3 | 10 | 90 |
| 17 | SiC | 0.1 | 6.2 | 510 | 8 | 8 | 92 |
| 18 | SiC | 0.1 | 6.2 | 550 | 12 | 2 | 98 |
| 19 | a-alumina | 0.1 | 16.3 | 400 | 17 | 76 | 24 |
| 19 | a-alumina | 0.1 | 16.3 | 500 | 27 | 65 | 35 |
| 20 | ZnO | 0.1 | 10.6 | 300 | 60 | 76 | 24 |
| 21 | ZnO | 0.1 | 10.6 | 350 | 73 | 82 | 18 |
| 22 | ZnO | 0.1 | 10.6 | 250 | 23 | 91 | 9 |

EXAMPLE 17

Nitrogen gas was introduced downflow to a 1"×18" 316 s.s. hot tube reactor system containing 67 ml of silicon carbide (SiC) at a total rate of 6.2 ml/min. The hot tube reactor was heated to 450° C. at which time 1-methoxyoctane (MO), obtained from hydrogenation of 1-methoxy-2,7-octadiene, was added downflow at 0.1 ml/min. Under these conditions 1-methoxyoctane was converted to a mixture of 1-octene and mixed internal octenes at 3.3% wt conversion with a selectivity to 1-octene of 10 m % and mixed internal octenes of 90 m %.

EXAMPLE 18

Example 17 was repeated with the exception that the temperature was 510° C. Under these conditions 1-methoxyoctane was converted to 1-octene in 8 m % selectivity at 8 m % conversion.

10.6 ml/min and temperature of 300° C. employed. Under these conditions 1-methoxyoctane was converted to 1-octene in 76 m % selectivity at 60 m % conversion.

EXAMPLE 22

Example 21 was repeated with the exception that a temperature of 350° C. was employed. Under these conditions 1-methoxyoctane was converted to 1-octene in 82 m % selectivity at 73 m % conversion.

EXAMPLE 23

Example 21 was repeated with the exception that a temperature of 250° C. was employed. Under these conditions 1-methoxyoctane was converted to 1-octene in 91 m % selectivity at 23 m % conversion.

Persons of ordinary skill in the art will recognize that many modifications may be made to the foregoing without departing from the spirit and scope thereof. The embodiment described herein is meant to be illustrative only and should not be taken as limiting the invention, which is defined in the following claims.

I claim:

1. A method for producing 1-octene from butadiene comprising:

dimerizing and alkoxylating butadiene in the presence of one or more alkoxy substituted phenyl phosphine ligands under alkoxydimerization conditions comprising an alkoxydimerization catalyst wherein said alkoxydimerization catalyst comprises a metal compound which is either soluble or superficially insoluble in said alkanol/ligand solution, said metal being selected from the group consisting of platinum, palladium, iridium, rhenium, ruthenium, and osmium, said alkoxydimerization conditions being effective to produce an alkoxydimerization product comprising one or more alkoxy substituted octadienes comprising primarily 1-alkoxy substituted octadiene;

hydrogenating the alkoxydimerization product under hydrogenation conditions effective to produce a hydrogenation product comprising primarily 1-alkoxy substituted octane; and, eliminating the alkoxy group from the hydrogenation product under elimination conditions effective to produce an elimination product comprising primarily 1-octene and a first alkanol having from about 1 to about 3 carbon atoms; and, separating said 1-octene from said elimination product.

2. The method of claim 1 wherein said first alkanol is methanol.

3. The method of claim 1 wherein said alkoxydimerization conditions comprise:

mixing said alkoxy substituted phenyl phosphine ligands with a second alkanol effective to produce an alkanol/ligand solution;

mixing an alkoxydimerization catalyst with said alkanol/ligand solution, producing an alkoxydimerization catalyst mixture;

subjecting said alkoxydimerization catalyst mixture to activation conditions comprising an activation time and an activation temperature effective to activate said alkoxydimerization catalyst, producing an activated catalyst mixture; and, adding an amount of butadiene to said activated catalyst mixture to produce a final alkoxylation/dimerization mixture, and subjecting said final alkoxylation/dimerization mixture to alkoxylation/dimerization conditions effective to alkoxylate and dimerize said butadiene to produce said elimination product.

4. The method of claim 3 wherein said second alkanol is the same as said first alkanol.

5. The method of claim 4 wherein said alkoxy substituted phenyl phosphine ligands are effective to form a product comprising 90 wt. % or more of the 1-alkoxy substituted octadiene.

6. The method of claim 3 wherein said alkoxy substituted phenyl phosphine ligands are effective to form a product comprising 90 wt. % or more of the 1-alkoxy substituted octadiene.

7. The method of claim 3 wherein:
said activation temperature is about 0° C. or more; and,
said activation time is about 1 minute or more.

8. The method of claim 3 wherein:
said activation temperature is about 25° C. or more; and,
said activation time is about 10 minutes.

9. The method of claim 3 wherein the amount of butadiene added is effective to produce a ratio of butadiene:alkanol of about 1:2 or greater on a molar basis.

10. The method of claim 3 wherein the amount of butadiene added is effective to produce a ratio of butadiene:alkanol is from about 1:2 to about 1:1.

11. The method of claim 10 further comprising:
cooling said activated catalyst mixture to about 0° C. or less, producing a cooled activated catalyst mixture; and
adding said amount of butadiene to said cooled activated catalyst mixture to produce said final alkoxydimerization mixture.

12. The method of claim 3 farther comprising:
cooling said activated catalyst mixture to about 0° C. or less, producing a cooled activated catalyst mixture; and
adding said amount of butadiene to said cooled activated catalyst mixture to produce said final alkoxydimerization mixture.

13. The method of claim 12 wherein said alkoxydimerization conditions comprise:

heating said final alkoxydimerization mixture to a preliminary temperature of about 25° .C or less, producing a preliminary heated final alkoxydimerization mixture; and heating said preliminary heated final alkoxydimerization to a final alkoxydimerization temperature and maintaining said final alkoxydimerization temperature for a time effective to produce said alkoxydimerization product.

14. The method of claim 13 wherein
said final alkoxydimerization temperature is about 60° C.; and,
said time effective to produce said alkoxydimerization product is about 2 hours or more.

15. The method of claim 14 wherein said alkoxydimerization time is about 8 hours or less.

16. The method of claim 3 farther comprising:
cooling said activated catalyst mixture to about −60° C., producing a cooled activated catalyst mixture; and
adding said amount of butadiene to said cooled activated catalyst mixture to produce said final alkoxydimerization mixture.

17. The method of claim 1 wherein said alkoxy substituted phenyl phosphine ligands are effective to form a product comprising 90 wt. % or more of the 1-alkoxy substituted octadiene.

18. The method of claim 1 wherein said alkoxy substituted phenyl phosphine ligands are selected from the group consisting of tris-(2,4,6,trimethoxy phenyl)phosphine and tris-(4-methoxyphenyl)phosphine.

19. The method of claim 1 wherein said alkoxyl substituted phenyl phosphine ligand is tris-(4-methoxyphenyl)phosphine.

20. The method of claim 1 wherein said alkoxydimerization catalyst comprises a metal compound which is either soluble or superficially insoluble in said alkanol/ligand solution, said metal being selected from the group consisting of palladium, platinum, and ruthenium.

21. The method of claim 20 wherein said noble metal compound comprises two noble metal atoms per molecule.

22. The method of claim 1 wherein said alkoxydimerization catalyst comprises a palladium compound which is either soluble or superficially insoluble in said alkanol/ligand solution.

23. The method of claim 1 wherein said noble metal compound comprises two noble metal atoms per molecule.

24. The method of claim 1 wherein said alkoxydimerization catalyst comprises a recycled stream from the alkoxydimerization process.

25. The method of claim 1 wherein the alkoxydimerization catalyst mixture comprises from about 0.005% mole to about 0.1% mole noble metal.

26. The method of claim 1 wherein said hydrogenation catalyst comprises a heterogeneous fixed bed.

27. The method of claim 26 wherein said elimination conditions comprise an elimination catalyst comprising metal oxide.

28. The method of claim 27 wherein said metal oxide is zinc oxide.

29. The method of claim 27 wherein said metal oxide is alpha alumina.

30. The method of claim 29 wherein said alpha alumina further comprises cesium.

31. The method of claim 1 wherein said elimination conditions comprise an elimination catalyst comprising metal oxide.

32. The method of claim 31 wherein said metal oxide is zinc oxide.

33. The method of claim 31 wherein said metal oxide is alpha alumina.

34. The method of claim 33 wherein said metal oxide further comprises a metal selected from the group consisting of Li, Na, K, Rb, and Cs and combinations thereof.

35. The method of claim 33 wherein said alpha alumina further comprises cesium.

36. The method of claim 31 wherein said elimination conditions comprise an elimination temperature effective to produce selectivity to 1-octene of 80 % or more.

37. The method of claim 36 wherein:
when said elimination catalyst is Cs-doped alpha alumina, said elimination temperature is from about 350° C. to about 600° C.; and
when said elimination catalyst is zinc oxide, said elimination temperature is from about 250° C. to about 400° C.

38. The method of claim 36 wherein:
when said elimination catalyst is Cs-doped alpha alumina, said elimination temperature is from about 250° C. to about 400° C.; and
when said elimination catalyst is zinc oxide, said elimination temperature is about 250° C.

39. The method of claim 36 wherein said elimination catalyst is zinc oxide and said elimination conditions comprise an elimination temperature of about 250° C.

40. The method of claim 36 wherein said separating said 1-octene from said elimination product comprises distilling said elimination product under distillation conditions effective to separate said 1-octene.

41. The method of claim 31 wherein said separating said 1-octene from said elimination product comprises distilling said elimination product under distillation conditions effective to separate said 1-octene.

42. The method of claim 1 wherein said hydrogenation conditions comprise a hydrogen gas comprising one or more additional inert gases.

43. The method of claim 1 wherein said elimination conditions comprise an elimination temperature effective to produce selectivity to 1-octene of 80 mole %.

44. The method of claim 1 wherein said elimination conditions comprise an elimination temperature effective to produce selectivity to 1-octene of 90 mole %.

45. The method of claim 1 wherein said alkoxydimerization conditions comprise recycling said alkanol to the alkoxydimerization.

46. The method of claim 1 wherein said separating said 1-octene from said elimination product comprises distilling said elimination product under distillation conditions effective to separate said 1-octene.

47. The method of claim 1 wherein said elimination conditions comprise purging said elimination catalyst with an inert gas prior eliminating the alkoxy group from the hydrogenation product.

48. The method of claim 47 wherein said inert gas is selected from the group consisting of nitrogen and argon.

49. The method of claim 48 wherein said purging comprises introducing said inert gas downflow at a flow rate of from about 1 to about 10 ml/min.

50. A method for producing 1-octene from butadiene comprising:
dimerizing and alkoxylating butadiene in the presence of one or more alkoxy substituted phenyl phosphine ligands under alkoxydimerization conditions comprising an alkoxydimerization catalyst comprising a noble metal compound which is either soluble or superficially insoluble in an alkanol/ligand solution, said noble metal being selected from the group consisting of platinum, palladium, iridium, rhenium, ruthenium, and osmium, said alkoxydimerization conditions being effective to produce an alkoxydimerization product comprising one or more alkoxy substituted octadienes comprising primarily 1-alkoxy substituted octadiene;
hydrogenating the alkoxydimerization product under hydrogenation conditions effective to produce a hydrogenation product comprising primarily 1-alkoxy substituted octane, said hydrogenation conditions comprising heterogeneous fixed bed hydrogenation catalyst;
eliminating the alkoxy group from the hydrogenation product under elimination conditions comprising an elimination catalyst comprising a metal oxide and an elimination temperature effective to produce selectivity to 1-octene of 80 mole % or more under said elimination conditions, producing an elimination product comprising a first alkanol having from about 1 to about 3 carbon atoms; and,
separating said 1-octene from said elimination product.

51. The method of claim 50 wherein said first alkanol is methanol.

52. The method of claim 50 wherein said alkoxydimerization conditions comprise:
mixing said alkoxy substituted phenyl phosphine ligands with a second alkanol effective to produce an alkanol/ligand solution;
mixing an alkoxydimerization catalyst with said alkanol/ligand solution, producing an alkoxydimerization catalyst mixture;
subjecting said alkoxydimerization catalyst mixture to activation conditions comprising an activation time and an activation temperature effective to activate said alkoxydimerization catalyst, producing an activated catalyst mixture; and,
adding an amount of butadiene to said activated catalyst mixture to produce a final alkoxylation/dimerization mixture, and subjecting said final alkoxylation/dimerization mixture to alkoxylation/dimerization conditions effective to alkoxylate and dimerize said butadiene to produce said elimination product.

53. The method of claim 51 wherein said alkoxydimerization conditions comprise:
mixing said alkoxy substituted phenyl phosphine ligands with a second alkanol effective to produce an alkanol/ligand solution;

mixing an alkoxydimerization catalyst with said alkanol/ligand solution, producing an alkoxydimerization catalyst mixture;

subjecting said alkoxydimerization catalyst mixture to activation conditions comprising an activation time and an activation temperature effective to activate said alkoxydimerization catalyst, producing an activated catalyst mixture; and, adding an amount of butadiene to said activated catalyst mixture to produce a final alkoxylation/dimerization mixture, and subjecting said final alkoxylation/dimerization mixture to alkoxylation/dimerization conditions effective to alkoxylate and dimerize said butadiene to produce said elimination product.

54. The method of claim 53 wherein said second alkanol is the same as said first alkanol.

55. The method of claim 50 wherein said alkoxydimerization conditions are effective to produce a product comprising 90 wt. % or more of the 1-alkoxy substituted octadiene.

56. The method of claim 51 wherein said alkoxydimerization conditions are effective to produce a product comprising 90 wt. % or more of the 1-alkoxy substituted octadiene.

57. The method of claim 52 wherein said alkoxydimerization conditions are effective to produce a product comprising 90 wt. % or more of the 1-alkoxy substituted octadiene.

58. The method of claim 53 wherein said alkoxydimerization conditions are effective to produce a product comprising 90 wt. % or more of the 1-alkoxy substituted octadiene.

59. The method of claim 54 wherein said alkoxydimerization conditions are effective to produce a product comprising 90 wt. % or more of the 1-alkoxy substituted octadiene.

60. The method of claim 59 wherein said alkoxydimerization conditions comprise a quantity of from about 0.8 moles to about 1.2 moles of said one or more alkoxy substituted phenyl phosphine ligands.

61. The method of claim 50 wherein said alkoxy substituted phenyl phosphine ligands are selected from the group consisting of tris-(2,4,6,trimethoxy phenyl)phosphine and tris-(4-methoxyphenyl)phosphine.

62. The method of claim 51 wherein said alkoxy substituted phenyl phosphine ligands are selected from the group consisting of tris-(2,4,6,trimethoxy phenyl)phosphine and tris-(4-methoxyphenyl)phosphine.

63. The method of claim 52 wherein said alkoxy substituted phenyl phosphine ligands are selected from the group consisting of tris-(2,4,6,trimethoxy phenyl)phosphine and tris-(4-methoxyphenyl)phosphine.

64. The method of claim 54 wherein said alkoxy substituted phenyl phosphine ligands are selected from the group consisting of tris-(2,4,6,trimethoxy phenyl)phosphine and tris-(4-methoxyphenyl)phosphine.

65. The method of claim 59 wherein said alkoxy substituted phenyl phosphine ligands are selected from the group consisting of tris-(2,4,6,trimethoxy phenyl)phosphine and tris-(4-methoxyphenyl)phosphine.

66. The method of claim 50 wherein said noble metal compound comprises a palladium compound.

67. The method of claim 51 wherein said alkoxydimerization catalyst comprises a palladium compound.

68. The method of claim 59 wherein said noble metal compound comprises a palladium compound.

69. The method of claim 50 wherein said noble metal compound comprises two noble metal atoms per molecule.

70. The method of claim 51 wherein said noble metal compound comprises two noble metal atoms per molecule.

71. The method of claim 52 wherein said noble metal compound comprises two noble metal atoms per molecule.

72. The method of claim 59 wherein said noble metal compound comprises two noble metal atoms per molecule.

73. The method of claim 68 wherein said noble metal compound comprises two noble metal atoms per molecule.

74. The method of claim 50 wherein said alkoxydimerization catalyst is tris(dibenzylideneacetone)di noble metal.

75. The method of claim 51 wherein said alkoxydimerization catalyst is tris(dibenzylideneacetone)dipalladium.

76. The method of claim 52 wherein said alkoxydimerization catalyst is tris(dibenzylideneacetone)dipalladium.

77. The method of claim 54 wherein said alkoxydimerization catalyst is tris(dibenzylideneacetone)dipalladium.

78. The method of claim 59 wherein said alkoxydimerization catalyst is tris(dibenzylideneacetone)dipalladium.

79. The method of claim 50 wherein said alkoxydimerization catalyst comprises a recycled stream from the alkoxydimerization process.

80. The method of claim 50 wherein the alkoxydimerization catalyst mixture comprises from about 0.005% mole to about 0.1% mole noble metal.

81. The method of claim 78 wherein the alkoxydimerization catalyst mixture comprises from about 0.005% mole to about 0.1% mole noble metal.

82. The method of claim 50 wherein the alkoxydimerization catalyst mixture comprises from about 0.01% mole to about 0.05% mole noble metal.

83. The method of claim 78 wherein the alkoxydimerization catalyst mixture comprises from about 0.01% mole to about 0.05% mole metal.

84. The method of claim 57 wherein:
said activation temperature is about 0° C. or more; and,
said activation time is about 1 minute or more.

85. The method of claim 58 wherein:
said activation temperature is about 0° C. or more; and,
said activation time is about 1 minute or more.

86. The method of claim 63 wherein:
said activation temperature is about 0° C. or more; and,
said activation time is about 1 minute or more.

87. The method of claim 78 wherein:
said activation temperature is about 0° C. or more; and,
said activation time is about 1 minute or more.

88. The method of claim 87 wherein said activation temperature is about 25° C.

89. The method of claim 87 wherein said activation time is about 10 minutes.

90. The method of claim 88 wherein said activation time is about 10 minutes.

91. The method of claim 52 wherein the amount of butadiene added is effective to produce a ratio of butadiene:alkanol is from about 1:2 to about 1:1.

92. The method of claim 90 wherein the amount of butadiene added is effective to produce a ratio of butadiene:alkanol is from about 1:2 to about 1:1.

93. The method of claim 52 farther comprising:
cooling said activated catalyst mixture to about 0° C. or less, producing a cooled activated catalyst mixture; and
adding said amount of butadiene to said cooled activated catalyst mixture to produce said final alkoxydimerization mixture.

94. The method of claim 52 further comprising:
cooling said activated catalyst mixture to about −60° C., producing a cooled activated catalyst mixture; and
adding said amount of butadiene to said cooled activated catalyst mixture to produce said final alkoxydimerization mixture.

95. The method of claim 78 further comprising:
cooling said activated catalyst mixture to about 0° C. or less, producing a cooled activated catalyst mixture; and
adding said amount of butadiene to said cooled activated catalyst mixture to produce said final alkoxydimerization mixture.

96. The method of claim 87 further comprising:
cooling said activated catalyst mixture to about 0° C. or less, producing a cooled activated catalyst mixture; and
adding said amount of butadiene to said cooled activated catalyst mixture to produce said final alkoxydimerization mixture.

97. The method of claim 90 further comprising:
cooling said activated catalyst mixture to about −60° C., producing a cooled activated catalyst mixture; and
adding said amount of butadiene to said cooled activated catalyst mixture to produce said final alkoxydimerization mixture.

98. The method of claim 93 wherein said alkoxydimerization conditions comprise:
heating said final alkoxydimerization mixture to a preliminary temperature of about 25° C. or less, producing a preliminary heated final alkoxydimerization mixture; and
heating said preliminary heated final alkoxydimerization to a final alkoxydimerization temperature and maintaining said final alkoxydimerization temperature for a time effective to produce said alkoxydimerization product.

99. The method of claim 94 wherein said alkoxydimerization conditions comprise:
heating said final alkoxydimerization mixture to a preliminary temperature of about 25° C. or less, producing a preliminary heated final alkoxydimerization mixture; and
heating said preliminary heated final alkoxydimerization to a final alkoxydimerization temperature and maintaining said final alkoxydimerization temperature for a time effective to produce said alkoxydimerization product.

100. The method of claim 97 wherein said alkoxydimerization conditions comprise:
heating said final alkoxydimerization mixture to a preliminary temperature of about 25° C. or less, producing a preliminary heated final alkoxydimerization mixture; and
heating said preliminary heated final alkoxydimerization to a final alkoxydimerization temperature and maintaining said final alkoxydimerization temperature for a time effective to produce said alkoxydimerization product.

101. The method of claim 98 wherein said alkoxydimerization time is from about 2 hours to about 8 hours.

102. The method of claim 99 wherein said alkoxydimerization time is from about 2 hours to about 8 hours.

103. The method of claim 100 wherein said alkoxydimerization time is from about 2 hours to about 8 hours.

104. The method of claim 103 wherein said effective alkoxydimerization pressure is from about 5 atmospheres to about 20 atmospheres.

105. The method of claim 103 wherein said effective alkoxydimerization pressure is from about 1 atmospheres to about 20 atmospheres.

106. The method of claim 102 further comprising cooling said final alkoxydimerization mixture once said alkoxydimerization time has passed to a temperature of about 25° C. or less, producing a cooled final alkoxydimerization mixture.

107. The method of claim 106 further comprising depressurizing said cooled final alkoxydimerization mixture, producing said alkoxydimerization product.

108. The method of claim 103 further comprising cooling said final alkoxydimerization mixture once said alkoxydimerization time has passed to a temperature of about 25° C. or less, producing a cooled final alkoxydimerization mixture.

109. The method of claim 108 further comprising depressurizing said cooled final alkoxydimerization mixture, producing said alkoxydimerization product.

110. The method of claim 107 further comprising recovering octadienes from said alkoxydimerization product before hydrogenating said alkoxydimerization product.

111. The method of claim 50 wherein said metal oxide is zinc oxide.

112. The method of claim 107 wherein said metal oxide is zinc oxide.

113. The method of claim 109 wherein said metal oxide is zinc oxide.

114. The method of claim 50 wherein said metal oxide comprises cesium-doped alpha alumina.

115. The method of claim 107 wherein said metal oxide further comprises cesium-doped alpha alumina.

116. The method of claim 109 wherein said metal oxide further comprises cesium-doped alpha alumina.

117. The method of claim 113 wherein said elimination catalyst is purged with an inert gas before introducing said hydrogenation product.

118. The method of claim 116 wherein said elimination catalyst is purged with an inert gas before introducing said hydrogenation product.

119. The method of claim 50 wherein said alkoxydimerization conditions comprise recycling said alkanol to the alkoxydimerization.

120. The method of claim 117 wherein said alkoxydimerization conditions comprise recycling said alkanol to the alkoxydimerization.

121. The method of claim 118 wherein said alkoxydimerization conditions comprise recycling said alkanol to the alkoxydimerization.

122. The method of claim 114 wherein said elimination temperature is from about 250° C. to about 600° C.

123. The method of claim 116 wherein said elimination temperature is from about 250° C. to about 600° C.

124. The method of claim 114 wherein said elimination temperature is from about 400° C. to about 550° C.

125. The method of claim 116 wherein said elimination temperature is from about 400° C. to about 550° C.

126. The method of claim 111 wherein said elimination temperature is from about 250° C. to about 400° C.

127. The method of claim 113 wherein said elimination temperature is from about 250° C. to about 400° C.

128. The method of claim 111 wherein said elimination conditions comprise an elimination temperature is about 250° C.

129. The method of claim 111 wherein said elimination conditions comprise an elimination temperature is about 250° C.

130. The method of claim 112 wherein said elimination conditions comprise an elimination temperature is about 250° C.

131. The method of claim 113 wherein said elimination conditions comprise an elimination temperature is about 250° C.

132. The method of claim 50 wherein said elimination conditions comprise a pressure of from about 0.8 atm to 1.2 atm.

133. The method of claim 121 wherein said elimination conditions comprise a pressure of from about 0.8 atm to 1.2 atm.

134. The method of claim 50 wherein said separating said 1-octene from said elimination product comprises distilling said elimination product under distillation conditions effective to separate said 1-octene.

135. The method of claim 94 wherein said separating said 1-octene from said elimination product comprises distilling said elimination product under distillation conditions effective to separate said 1-octene.

136. The method of claim 97 wherein said separating said 1-octene from said elimination product comprises distilling said elimination product under distillation conditions effective to separate said 1-octene.

137. The method of claim 109 wherein said separating said 1-octene from said elimination product comprises distilling said elimination product under distillation conditions effective to separate said 1-octene.

138. A method for producing 1-octene from butadiene comprising:
   dimerizing and alkoxylating butadiene in the presence of tris-(4-methoxyphenyl) phosphine under alkoxydimerization conditions comprising tris(dibenzylideneacetone)dipalladium as an alkoxydimerization catalyst, said alkoxydimerization conditions being effective to produce an alkoxydimerization product comprising one or more alkoxy substituted octadienes comprising primarily 1-alkoxy substituted octadiene, said alkoxy having from about 1 to about 3 carbon atoms;
   hydrogenating the alkoxydimerization product under hydrogenation conditions effective to produce a hydrogenation product comprising primarily 1-alkoxy substituted octane, said hydrogenation conditions comprising heterogeneous fixed bed hydrogenation catalyst;
   eliminating the alkoxy group from the hydrogenation product under elimination conditions effective to produce selectivity to 1-octene of 80 mole % or more, said elimination conditions comprising an elimination catalyst selected from the group consisting of zinc oxide and cesium doped alpha alumina; and
   separating said 1-octene from said elimination product.

139. The method of claim 138 wherein said alkoxy is methoxy.

140. A method for producing 1-octene from butadiene comprising:
   dimerizing and alkoxylating butadiene in the presence of tris-(4-methoxyphenyl)phosphine under alkoxydimerization conditions comprising tris(dibenzylideneacetone)dipalladium as an alkoxydimerization catalyst, said alkoxydimerization conditions being effective to produce an alkoxydimerization product comprising one or more alkoxy substituted octadienes comprising primarily 1-alkoxy substituted octadiene, said alkoxy having from about 1 to about 3 carbon atoms;
   said dimerizing and alkoxylating butadiene comprising:
      mixing said tris-(4-methoxyphenyl)phosphine with a second alkanol effective to produce an alkanol/ligand solution;
      mixing said tris(dibenzylideneacetone)dipalladium with said alkanol/ligand solution, producing an alkoxydimerization catalyst mixture;
      subjecting said alkoxydimerization catalyst mixture to activation conditions comprising an activation time and an activation temperature effective to activate said alkoxydimerization catalyst, producing an activated catalyst mixture;
      cooling said activated catalyst mixture, producing to produce a cooled activated catalyst mixture; and
      adding an amount of butadiene to said cooled activated catalyst mixture to produce a final alkoxylation/dimerization mixture; and
   subjecting said final alkoxylation/dimerization mixture to alkoxylate/dimerization conditions effective to alkoxylate and dimerize said butadiene to produce said elimination product, said alkoxylation/dimerization conditions comprising:
      heating said final alkoxydimerization mixture to a preliminary temperature of about 25° C. or less, producing a preliminary heated final alkoxydimerization mixture;
      heating said preliminary heated final alkoxydimerization mixture to a final alkoxydimerization temperature and maintaining said final alkoxydimerization mixture at said final alkoxydimerization temperature at an effective alkoxydimerization pressure for an alkoxydimerization time of about 2 hours or more;
   hydrogenating the alkoxydimerization product under hydrogenation conditions effective to produce a hydrogenation product comprising primarily 1-alkoxy substituted octane, said hydrogenation conditions comprising a heterogeneous fixed bed hydrogenation catalyst; and,
   eliminating the alkoxy group from the hydrogenation product under elimination conditions effective to produce selectivity to 1-octene of 80 mole % or more, said elimination conditions comprising an elimination catalyst selected from the group consisting of zinc oxide and cesium doped alpha alumina; and,
   separating said 1-octene from said elimination product.

141. The method of claim 140 wherein said cooling said activated catalyst mixture comprises cooling said activated catalyst mixture to a temperature of about 0° C. or less.

142. The method of claim 140 wherein said cooling said activated catalyst mixture comprises cooling said activated catalyst mixture to a temperature of about −60° C.

143. The method of claim 140 wherein said elimination catalyst is zinc oxide.

144. The method of claim 141 wherein said elimination catalyst is zinc oxide.

145. The method of claim 142 wherein said elimination catalyst is zinc oxide.

146. The method of claim 140 wherein said alkoxy is methoxy.

147. The method of claim 141 wherein said alkoxy is methoxy.

148. The method of claim 142 wherein said alkoxy is methoxy.

149. The method of claim 143 wherein said alkoxy is methoxy.

150. The method of claim 144 wherein said alkoxy is methoxy.

151. The method of claim 145 wherein said alkoxy is methoxy.

152. The method of claim 140 wherein said alkoxydimerization conditions comprise a quantity of from about 0.8 moles to about 1.2 moles of said tris-(4-methoxyphenyl) phosphine.

153. The method of claim 151 wherein said alkoxydimerization conditions comprise a quantity of from about 0.8 moles to about 1.2 moles of said tris-(4-methoxyphenyl) phosphine.

154. The method of claim 151 wherein the alkoxydimerization catalyst mixture comprises from about 0.005% mole to about 0.1% mole noble metal.

155. The method of claim 153 wherein the alkoxydimerization catalyst mixture comprises from about 0.005% mole to about 0.1% mole noble metal.

156. The method of claim 140 wherein the alkoxydimerization catalyst mixture comprises from about 0.01% mole to about 0.05% mole noble metal.

157. The method of claim 153 wherein the alkoxydimerization catalyst mixture comprises from about 0.01% mole to about 0.05% mole noble metal.

158. The method of claim 140 wherein said activation conditions comprise:
an activation temperature of about 0° C. or more; and,
an activation time of about 1 minute or more.

159. The method of claim 140 wherein said activation conditions comprise:
an activation temperature of about 25° C. or more; and,
an activation time of about 10 minutes.

160. The method of claim 151 wherein said activation conditions comprise:
an activation temperature of about 0° C. or more; and,
an activation time of about 1 minute or more.

161. The method of claim 151 wherein said activation conditions comprise:
an activation temperature of about 25° C. or more; and,
an activation time of about 10 minutes.

162. The method of claim 153 wherein said activation conditions comprise:
an activation temperature of about 0° C. or more; and,
an activation time of about 1 minute or more.

163. The method of claim 153 wherein said activation conditions comprise:
an activation temperature of about 25° C. or more; and,
an activation time of about 10 minutes.

164. The method of claim 157 wherein said activation conditions comprise:
an activation temperature of about 0° C. or more; and,
an activation time of about 1 minute or more.

165. The method of claim 157 wherein said activation conditions comprise:
an activation temperature of about 25° C. or more; and,
an activation time of about 10 minutes.

166. The method of claim 140 wherein the amount of butadiene added is effective to produce a ratio of butadiene: alkanol of about 1:2 or greater on a molar basis.

167. The method of claim 140 wherein the amount of butadiene added is effective to produce a ratio of butadiene: alkanol is from about 1:2 to about 1:1.

168. The method of claim 151 wherein the amount of butadiene added is effective to produce a ratio of butadiene: alkanol is from about 1:2 to about 1:1.

169. The method of claim 153 wherein the amount of butadiene added is effective to produce a ratio of butadiene: alkanol is from about 1:2 to about 1:1.

170. The method of claim 165 wherein the amount of butadiene added is effective to produce a ratio of butadiene: alkanol of about 1:2 or greater on a molar basis.

171. The method of claim 165 wherein the amount of butadiene added is effective to produce a ratio of butadiene: alkanol is from about 1:2 to about 1:1.

172. The method of claim 140 wherein said heating said final alkoxydimerization mixture to a preliminary temperature comprises heating to a temperature of about 25° C. or less.

173. The method of claim 172 wherein said alkoxydimerization time is about 4 hours or more.

174. The method of claim 173 wherein said alkoxydimerization time is about 8 hours or less.

175. The method of claim 174 wherein said effective alkoxydimerization conditions comprise an alkoxydimerization pressure of from about 5 atmospheres to about 20 atmospheres.

176. The method of claim 171 wherein said heating said final alkoxydimerization mixture to a preliminary temperature comprises heating to a temperature of about 25° C. or less.

177. The method of claim 176 wherein said alkoxydimerization time is about 4 hours or more.

178. The method of claim 177 wherein said alkoxydimerization time is about 8 hours or less.

179. The method of claim 178 wherein said effective alkoxydimerization pressure is from about 5 atmospheres to about 20 atmospheres.

180. The method of claim 178 wherein said effective alkoxydimerization pressure is from about 1 atmospheres to about 20 atmospheres.

181. The method of claim 140 wherein said separating said 1-octene from said elimination product comprises distilling said elimination product under distillation conditions effective to separate said 1-octene.

182. The method of claim 171 wherein said separating said 1-octene from said elimination product comprises distilling said elimination product under distillation conditions effective to separate said 1-octene.

183. The method of claim 180 wherein said elimination conditions comprise purging said elimination catalyst with an inert gas prior eliminating the alkoxy group from the hydrogenation product.

184. The method of claim 183 wherein said inert gases is selected from the group consisting of nitrogen and argon.

185. The method of claim 184 wherein said purging comprises introducing said inert gas downflow at a flow rate of from about 1 to about 10 ml/min.

186. The method of claim 185 wherein said flow rate is about 6.2 ml/min.

187. A method for producing 1-octene from butadiene comprising:
dimerizing and methoxylating butadiene in the presence of tris-(4-methoxyphenyl) phosphine under methoxydimerization conditions comprising tris(dibenzylideneacetone)dipalladium as a methoxydimerization catalyst, said methoxydimerization conditions being effective to produce a methoxydimerization product comprising one or more methoxy substituted octadienes comprising primarily 1-methoxy substituted octadiene;
said dimerizing and methoxylating butadiene comprising:
mixing said tris-(4-methoxyphenyl)phosphine with an alkanol comprising methanol effective to produce a methanol/ligand solution;
mixing said tris(dibenzylideneacetone)dipalladium with said methanol/ligand solution, producing a methoxydimerization catalyst mixture comprising from about 0.005% mole to about 0.1% mole noble metal;
subjecting said methoxydimerization catalyst mixture to activation conditions comprising an activation time of about 10 minutes and an activation temperature of about 25° C. or more, said activation conditions being effective to activate said methoxydimerization catalyst, producing an activated catalyst mixture;
cooling said activated catalyst mixture to a temperature of about −60° C., producing to produce a cooled activated catalyst mixture; and
adding an amount of butadiene to said cooled activated catalyst mixture to produce a final methoxylation/ dimerization mixture, said amount of butadiene being effective to produce a ratio of butadiene:alkanol of about 1:2 or greater on a molar basis; and subjecting said final methoxylation/dimerization mixture to methoxylation/dimerization conditions effective to methoxylate and dimerize said butadiene to produce said elimination product, said methoxylation/dimerization conditions comprising:

heating said final methoxydimerization mixture to a preliminary temperature of about 25° C. or less, producing a preliminary heated final methoxydimerization mixture;

heating said preliminary heated final methoxydimerization mixture at an effective methoxydimerization pressure to a final methoxydimerization temperature for a methoxydimerization time of from about 2 to about 8 hours;

hydrogenating the methoxydimerization product under hydrogenation conditions effective to produce a hydrogenation product comprising primarily 1-methoxy substituted octane, said hydrogenation conditions comprising a heterogeneous fixed bed hydrogenation catalyst; and, eliminating the methoxy group from the hydrogenation product under elimination conditions effective to produce methanol and selectivity to 1-octene of 80 mole % or more, said elimination conditions comprising an elimination catalyst comprising zinc oxide;

separating said 1-octene from said elimination product; and recycling said methanol to said dimerizing and methoxylating process.

188. The method of claim 187 wherein said alkoxydimerization conditions comprise a quantity of from about 0.8 moles to about 1.2 moles of said tris-(4-methoxyphenyl) phosphine.

189. The method of claim 187 wherein the methoxydimerization catalyst mixture comprises from about 0.01% mole to about 0.05% mole noble metal.

190. The method of claim 188 wherein the alkoxydimerization catalyst mixture comprises from about 0.01% mole to about 0.05% mole noble metal.

191. The method of claim 187 wherein the amount of butadiene added is effective to produce a ratio of butadiene: alkanol is from about 1:2 to about 1:1.

192. The method of claim 188 wherein the amount of butadiene added is effective to produce a ratio of butadiene: alkanol is from about 1:2 to about 1:1.

193. The method of claim 189 wherein the amount of butadiene added is effective to produce a ratio of butadiene: alkanol is from about 1:2 to about 1:1.

194. The method of claim 190 wherein the amount of butadiene added is effective to produce a ratio of butadiene: alkanol of about 1:2 or greater on a molar basis.

195. The method of claim 190 wherein said effective alkoxydimerization conditions comprise an alkoxydimerization pressure of from about 5 atmospheres to about 20 atmospheres.

196. The method of claim 190 herein said effective alkoxydimerization pressure is from about 1 atmospheres to about 20 atmospheres.

197. The method of claim 196 wherein said separating said 1-octene from said elimination product comprises distilling said elimination product under distillation conditions effective to separate said 1-octene.

198. The method of claim 197 wherein said elimination conditions comprise purging said elimination catalyst with an inert gas prior eliminating the alkoxy group from the hydrogenation product.

199. The method of claim 198 wherein said inert gases is selected from the group consisting of nitrogen and argon.

200. The method of claim 199 wherein said purging comprises introducing said inert gas downflow at a flow rate of from about 1 to about 10 ml/min.

201. The method of claim 200 wherein said flow rate is about 6.2 ml/min.

* * * * *